(12) United States Patent
Montagnino et al.

(10) Patent No.: US 6,416,534 B1
(45) Date of Patent: Jul. 9, 2002

(54) PORTABLE HEATING PAD WITH REMOVABLE HEAT PAD, REMOVABLE GEL PACK AND PRESSURE BLADDER

(75) Inventors: James Montagnino, St. Charles; Arnold V. DeCarlo, Manhattan, both of IL (US)

(73) Assignee: Sunbeam Products, Inc., Boca Raton, FL (US)

( * ) Notice: Subject to any disclaimer, the term of this patent is extended or adjusted under 35 U.S.C. 154(b) by 16 days.

(21) Appl. No.: 09/685,174

(22) Filed: Oct. 10, 2000

(51) Int. Cl.[7] .................................................. A61F 7/00
(52) U.S. Cl. ........................ 607/114; 128/82.1; 602/6
(58) Field of Search .................. 607/114; 128/82.1; 602/18–20, 6, 26–29

(56) References Cited

U.S. PATENT DOCUMENTS

| | | |
|---|---|---|
| 891,181 A | 6/1908 | Mitchell |
| 2,573,791 A | 11/1951 | Howells |
| 2,823,668 A | 2/1958 | Van Court et al. |
| 3,561,435 A | 2/1971 | Nicholson |
| 3,785,375 A | 1/1974 | Lipson |
| 4,542,285 A | 9/1985 | Grise |
| 4,633,068 A | 12/1986 | Grise |
| 4,677,970 A | 7/1987 | Green et al. |
| 4,702,235 A | 10/1987 | Hong |
| 4,753,240 A | 6/1988 | Sparks |
| 4,846,176 A | 7/1989 | Golden |
| 5,002,047 A * | 3/1991 | Sandvig et al. ................ 602/8 |
| 5,007,416 A | 4/1991 | Burns et al. |
| 5,030,402 A * | 7/1991 | Zachariades ................ 264/138 |
| 5,050,595 A | 9/1991 | Krafft |
| 5,195,945 A * | 3/1993 | Sandvig et al. ................ 602/8 |
| 5,336,255 A | 8/1994 | Kanare et al. |
| RE34,883 E | 3/1995 | Grim |
| 5,407,421 A | 4/1995 | Goldsmith |
| 5,432,322 A | 7/1995 | Ingram et al. |
| 5,450,858 A | 9/1995 | Zablotsky et al. |
| 5,601,264 A * | 2/1997 | Peart ........................ 248/118.1 |
| 5,695,452 A | 12/1997 | Grim et al. |
| 5,800,490 A | 9/1998 | Patz et al. |
| 5,817,145 A | 10/1998 | Augustine et al. |
| 5,826,841 A * | 10/1998 | Lavore ........................ 248/118 |
| 5,835,983 A | 11/1998 | McMahen et al. |
| 6,165,208 A | 12/2000 | Reyes et al. |

OTHER PUBLICATIONS

Product Sell Sheet For Cold Pack—Model 1751–8—(1999).

Product Sell Sheet For Heat To Go—Large Heat Wrap—Model 1763–8—(1999).

Product Sell Sheet For Heat To Go—Medium Heat Wrap—Model 1762–8—(1999).

Product Sell Sheet For Heat To Go—Heat Wrap—Model 1761–8—(1999).

Product Sell Sheet For Heat To Go—Small Heat Wrap—Model 1760–8—(1999).

\* cited by examiner

*Primary Examiner*—Michael Powell Buiz
*Assistant Examiner*—Meredith H. Schoenfeld
(74) *Attorney, Agent, or Firm*—Kramer, Levin, Naftalis & Frankel, LLP

(57) ABSTRACT

The present invention provides a portable heating pad capable of transferring heat to an anatomical region of a subject by means of a removable gel pack member which is releasably attached to a heat pad member with a detachable electrical power cord. The present invention can also include an inflatable bladder having an integrally formed pump. The portable heating pads of the present invention are useful for the rapid and convenient treatment of various muscular and orthopedic aches and pains of a mobile subject.

25 Claims, 6 Drawing Sheets

PORTABLE HEATING PAD WITH REMOVABLE HEAT PAD, REMOVABLE GEL PACK AND PRESSURE BLADDER

RELATED APPLICATIONS

The present application is related to U.S. patent application Ser. No. 09/441,282, filed Nov. 16, 1999, and U.S. patent application Ser. No. 09/471,599, filed Dec. 23, 1999 both of which are hereby incorporated by reference in their entirety.

FIELD OF THE INVENTION

The present invention relates generally to improvements in heating pads and particularly to portable heating pads having removable heat pads, removable gel packs and pressure bladders which provide warming capability.

BACKGROUND INFORMATION

The value of heat treatment for easing and preventing the onset of pain in muscle tissues is well established. For example, muscles which tend to cramp may be heated before strenuous exercise to enrich the blood supply to the appropriate areas. Means for effecting such heat treatment include the use of electrical heating pads and portable heating pads having reusable gel packs of the microwavable or chemical variety. Electrical heating pads are typically preferred over portable heating pads when heat treatment is needed over an extended period of time because electrical heating pads have a constant source of power and can achieve and maintain a maximum heat level. However, conventional electrical heating pads used in treating subjects in need of heat therapy suffer from the inconvenience of restricting the subject's physical location because of the power cord attachment. Portable heating pads using gel packs suffer from temperature decay problems because they do not have a constant power source allowing them to maintain maximum heat levels. Thus, they lose their therapeutic heating effect rapidly due to heat transfer to the targeted body part and the atmosphere.

Typical devices for administering such heat therapy comprise the aforementioned heat sources contained within a suitably shaped fabric holder with a means for wrapping the respective heat source around a targeted body part. However, the efficacy of the resulting treatment depends in part on the intimacy of contact achievable between the heat source and the target anatomical region. The usual means of controlling the intimacy of contact is simply adjusting the tightness of the wrapping of the fabric holder around the targeted area. Because of the intrinsic difficulty of wrapping the fabric holder with sufficient precision, the comfort of the user is adversely affected if too tightly wrapped, or the efficiency of heat thermal transfer is respectively reduced if too loosely wrapped.

The typical methods of achieving optimal contact are largely based on the use of materials having elastic properties in the construction of the wraps. Examples of such materials include natural and synthetic rubbers and other synthetic elastomers. This approach is however inherently limited since the elastic property of the construction material is diminished by pre-stretching during the initial wrapping, and therefore, restricts further adjustment of the tightness between the wrap and the targeted body part.

Another method of adjusting the contact between the wrap and the targeted body part is a therapeutic pad having a pressure bladder. Therapeutic pads having pressure bladders have made use of external hand pumps and are disclosed in Re. 34,883. Such therapeutic pads, however, are bulky to carry and operate.

SUMMARY OF THE INVENTION

The present invention provides an improved portable heating pad that overcomes the above-described deficiencies of known devices. In an exemplary embodiment, the present invention provides a heating pad comprising an outer base member with strap attachments which can be adjusted in length to the size of the subject's targeted body part, a removable heat pad which can be heated to a desired temperature prior to disconnecting the power cord, and a removable gel pack which can be heated to a desired temperature prior to attachment to the removable heat pad and thereby achieve more efficient extended thermal transfer. Having a removable heat pad with a connector allowing the power cord to be disconnected from the heating pad would allow the subject to be physically mobile after initial heat up of the heat pad. Such an enhanced design which affords heat therapy while allowing the subject physical mobility and a greater degree of control in the adjustment of the contact between the wrap and the targeted body part would enhance the comfort of the user as well as the efficiency of heat thermal transfer to the subject.

In a further embodiment, the present invention provides a portable heating pad comprising an outer base member having a layer of reflective material to reflect heat back to the removable heat pad and attached removable gel pack and the subject's targeted body part and thereby achieve more efficient extended thermal transfer.

In a further embodiment, the present invention provides a portable heating pad having a pressure bladder which can be pressurized to enhance the surface contact between the removable gel pack attached to the removable heat pad and a targeted body part and which can be inflated or deflated so as to adjust the tightness of fit between the removable gel pack attached to the removable heat pad and the subject's targeted body part. In an exemplary embodiment, the pressure bladder may be inflated using an internal manual pump which is integrated with the main body of the portable heating pad. Use of an internal manual pump which is integrated with the main body of the portable heating pad to inflate the pressure bladder so as to adjust the tightness of fit of the portable heating pad would be more compact and thus significantly more convenient to operate than pads using external pumps. Portable heating pads with pressure bladders utilizing such integrated hand pumps and with a disconnectable power source would therefore provide an enhanced mode of heat therapy to subjects in need of such therapy.

In a further embodiment, the present invention provides a portable heating pad comprising an outer base member with strap attachments which can be adjusted in length to the size of the subject's targeted body part, a removable heat pad member, and a removable gel pack member which is vertically divided into a plurality of discrete segments. Dividing the gel pack member into a plurality of discrete segments would enhance the flexibility of the gel pack and prevent the gel from squeezing out from the points of contact with the subject's targeted body part, thus preventing reduction of the mass of gel in contact with the targeted body part.

Accordingly, the present invention provides a portable heating pad for a subject in need of heat therapy comprising an outer base member wherein the outer base member comprises an outer layer of a heat reflective material and a resilient filler and an inner fabric cover and has strap attachments which can be adjusted in length to the size of the subject's targeted body part, a removable heat pad member comprising a cover and an electrical heating element, wherein the cover comprises an inner layer having a plurality of fasteners and an outer layer, a removable gel pack member which comprises a heat-retentive gel which contacts an anatomical portion of the subject and which contacts the heat pad member and is releasably attached to the inner layer of that member by a plurality of complementary positioned fasteners. The electrical heating element is enclosed by the cover of the removable heat pad member and is substantially evenly distributed within the cover. To afford the subject physical mobility, the present invention conveniently permits preliminary heating of the gel pack member to a predetermined temperature prior to attachment to the removable heat pad member. The present invention also allows heating of the heat pad member to a predetermined temperature prior to or after attachment of the removable gel pack member prior to disconnection of the power cord from the portable heating pad.

The accompanying drawings, referred to herein and constituting a part hereof, illustrate embodiments of the invention and, together with the description, serve to explain the principles of the invention.

Other features and advantages of the present invention will be apparent from the following description of the exemplary embodiments thereof, and from the claims.

In order that the present invention may be readily understood, embodiments thereof will now be described, by way of example, with reference to the accompanying drawings.

DETAILED DESCRIPTION

Figure 1:
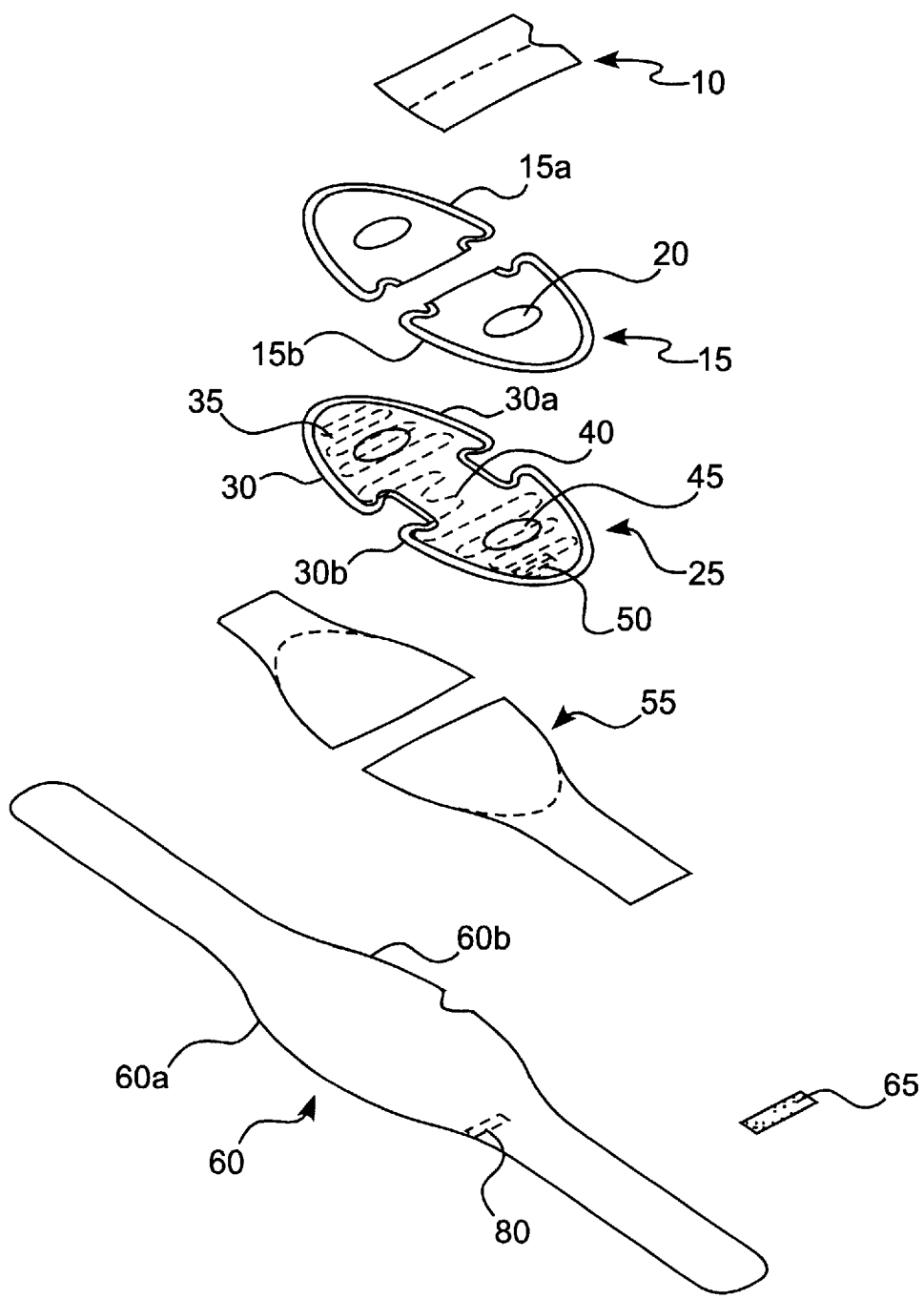
FIG. 1 is a perspective exploded view of an exemplary embodiment of an integrated portable heating pad (back wrap) with removable heat pad and removable gel pack in accordance with the present invention.

In accordance with an exemplary embodiment, a portable heating pad of the present invention includes a portable heating pad suitable for application to various anatomical regions of a subject's body including, for example, the back. Referring to FIG. 1, illustrating an exemplary embodiment of the present invention intended for application to the back, an outer base member 60 is shaped to conformably and substantially cover a portion of the back of a subject. Such a portable heating pad is constructed so as to have, for example, fastening closures 65 or 70 permanently attached to two oppositely disposed arm portions of the outer base member 60 and located so as to provide a releasable securement of the portable heating pad to or around the desired anatomical region of the subject's body.

Referring to FIG. 1, the fastening closures 65 and 70 comprise any type of appropriate fastener known in the art. Well adapted to the purpose is, for example, a hook or loop material such as Velcro™. Such hook or loop fasteners are located at positions on the outer base member 60 in the back wrap embodiment such that the respective complementary hook and loop fasteners are capable of approaching each other in space while creating a releasable, stable attachment to the pre-selected anatomical region of the subject's body to which the portable heating pad is affixed. The fasteners 65 and 70 are adjoined to the respective outer base member 60, for example, by means known to those skilled in the art, including for example, stitching, thermal welding and epoxy gluing. The junction so formed should be capable of withstanding the typical thermal and mechanical stresses expected for a portable heating pad.

In an exemplary embodiment, the outer base member 60 includes an outer cover 60b comprising a reflective material and a resilient filler (not shown) and an inner fabric cover 60a. The resilient filler, which is located between the outer cover 60b and the inner fabric cover 60a, is made of any of the typical filler materials used in portable heating pads, most typically a nonflammable fiber or other flame-resistant or flame-retardant materials. A useful and workable filler is a rubber sheet made from various types of rubber, but favorably selected from, for example, neoprene rubber, polyurethane and buna rubber. The outer cover 60b, which includes, for example, a reflective material, and the inner fabric cover 60a, which includes, for example, flexible fabric material, are permanently secured together along their perimeters by means known in the art, for example, by stitching, riveting, stapling, RF welding or ultrasonic welding. The reflective material of the outer cover and the flexible fabric material of the inner cover desirably comprise materials which resist the usual wear and tear resulting from normal use as portable heating pads. Suitable exemplary reflective materials include a flexible substrate onto which a metallized surface is deposited, for example, sputter-coated vinyl or mylar, woven metallized thread, for example, fine aluminum or stainless steel, which can be stitched to another fabric, such as nylon, or quilted vinyl material coated with foil. Suitable exemplary flexible fabric materials include nylon, cotton, cotton/polyester or lycra.

Figure 2:
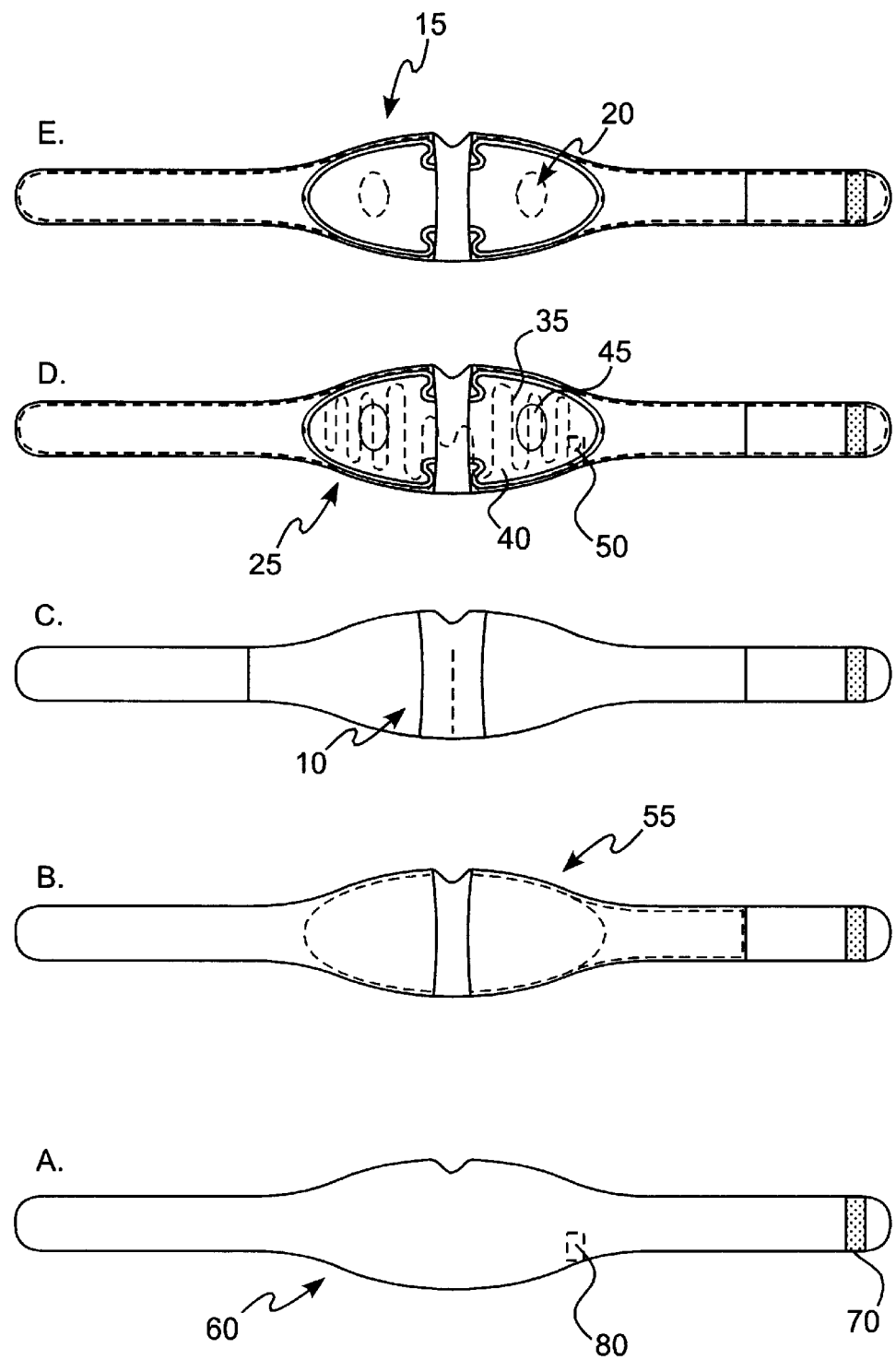
FIGS. 2A–E are a plan view of the stepwise assembly of an exemplary embodiment of an integrated portable heating pad with removable heat pad and removable gel pack in accordance with the present invention.

In accordance with the exemplary embodiment illustrated in the FIG. 1, the portable heating pad of the present invention includes a removable heat pad member 25 and a removable gel pack member 15. The removable heat pad member 25 can be releasably attached to the outer base member by means of, for example, a heat pad/gel pack pocket member 55. Placement of the heat pad member facilitates contact with the targeted anatomical region of the subject. As illustrated in FIGS. 1 and 2B–E, the removable heat pad member 25 is stably maintained within, for example, the heat pad/gel pack pocket 55. The heat pad/gel pack pocket 55 (or other suitable retention means) in which the removable heat pad member 25 is inserted during use of the portable heating pad of the present invention is, for example, permanently attached to the outer base member 60 by stitching or stapling, as illustrated in FIG. 2B.

FIGS. 2A–E illustrate the stepwise assembly of an exemplary embodiment of an integrated portable heating pad with removable heat pad and removable gel pack in accordance with the present invention. The heat pad/gel pack pocket 55 is attached to the outer base member (FIG. 2A) by stitching or stapling along the lines indicated on the outer base member in FIG. 2B. A flap 10 is attached to the heat pad/gel pack pocket 55 and outer base member 60 along the lines indicated in FIG. 2C. The removable heat pad is inserted into the heat pad/gel pack pocket as indicated in FIG. 2D. The removable gel pack can be attached to the removable heat pad before the removable heat pad is inserted into the heat pad/gel pack pocket as indicated in FIG. 2E.

Figure 3A:
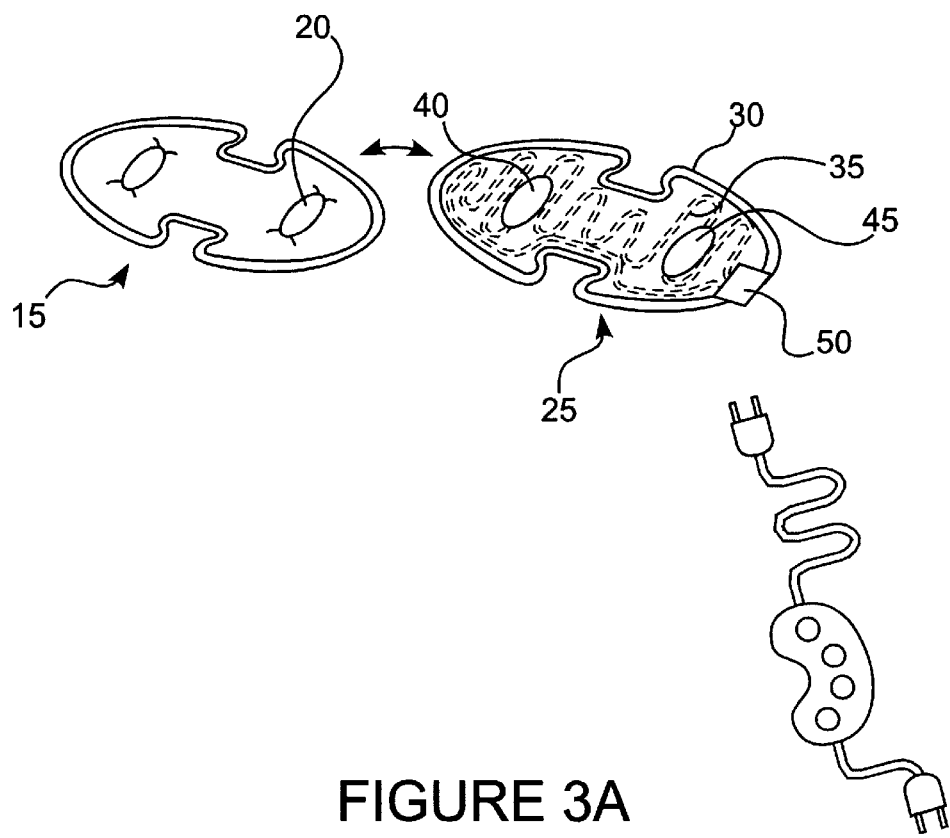
FIGS. 3A and 3B are cross-sectional diagrammatic and perspective views, respectively, of an embodiment of a removable heat pad and removable gel pack in accordance with the present invention.

The removable heat pad member 25 comprises a cover 30, padding 40, an electrical heating element 35, and a connector 50 for coupling to a detachable electrical cord 75. As shown in FIG. 3A, the detachable electrical cord 75 is coupled to a temperature controller having a plug for insertion into a suitable power source, such as a conventional household wall power outlet. The cover 30 comprises a first layer 30a and a second layer 30b. The first layer 30a is an inner layer which contacts substantially the entire outer layer 15b of the removable gel pack member 15 and provides an interface through which thermal energy passes to the gel pack member 15. The second layer 30b is an outer layer which provides the exterior surface of the removable heat pad member. Each layer 30a and 30b comprises a flexible fabric material and the layers are permanently secured together along their peripheral edges by means known in the art, for example, by stitching, riveting or stapling. One of the permanently secured perimeters of the heat pad member has a cut-out 80 for the connector 50 for the detachable electrical cord 75 with temperature controller and plug. Dispersed uniformly within the cover is the electrical heating element 35 which is connected to the connector 50 and padding 40. (FIG. 3A). The padding 40 consists of the typical filler materials used in electrical heating pads, typically made from a nonflammable fiber or other flame-resistant or flame-retardant materials.

The removable gel pack member 15 is releasably attached to the inner layer 30a of the cover of the removable heat pad member 25, and comprises a heat-retentive gel, which can be heated to a predetermined temperature prior to attachment to the removable heat pad member 25. In an exemplary embodiment of the present invention, the outer layer 15b of the removable gel pack 15 contacts and covers substantially the entire inner layer 30a of the cover 30 of the removable heat pad member 25, and provides an interface through which thermal energy flows from the heat pad member 25 to the gel pack member 15. The gel pack member 15 is typically constructed from two sheets (15a and 15b) of a thin liquid-impermeable flexible plastic, such as vinyl, nylon or polyethylene. The inner and outer sheets 15a and 15b are sealed along their peripheral edges by means known in the art, such as by thermal welding or sealing, and as such form a leak-proof container for the gel. In an exemplary embodiment, the inner layer 15a of the gel pack 15 provides the interior surface of the portable heating pad. Thus, when the gel pack member is placed in substantial contact with an anatomical portion of a subject in need of heat therapy, heat is transferred to the subject through the interface formed by inner layer 15a.

Figure 3B:
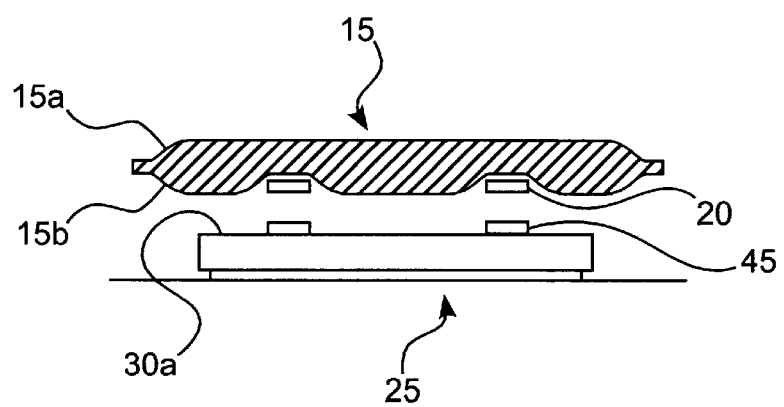

In an exemplary embodiment of the present invention, the removable gel pack member 15 is attached to the removable heat pad member 25 by two pairs of fasteners located respectively in complementary positions on the removable heat pad member and the removable gel pack (FIGS. 3A and 3B). In an exemplary embodiment, the outer layer 15b of the removable gel pack member 15 has attached thereto at least one fastener 20 which may, for example, be of a hook and loop type, such as Velcro™, placed in position(s) so as to fasten to complementary fasteners 45 positioned on the inner layer 30a of the removable heat pad member 25 and thereby to stably attach the removable gel pack 15 to the removable heat pad member 25. (see FIG. 3B). The fasteners 20 and 45 are permanently attached by any suitable method known in the art, such as by stitching, sewing, gluing, welding, riveting, etc.

Referring to FIG. 1, the removable gel pack 15 may be heated prior to use by any means consistent with the materials of which the gel pack is constructed. For example, the gel pack may be heated in a microwave oven to the predetermined temperature. Heating under an infrared heater is an alternative method of heating the removable gel pack 15.

Figure 4A:
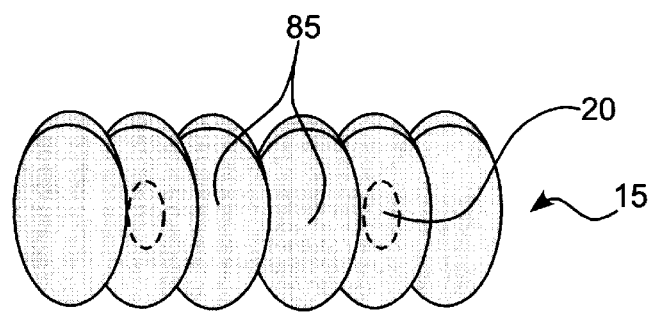
FIGS. 4A and 4B are perspective and cross-sectional views, respectively, of an embodiment of a removable gel pack with a plurality of discrete vertical segments in accordance with the present invention.
Figure 4B:
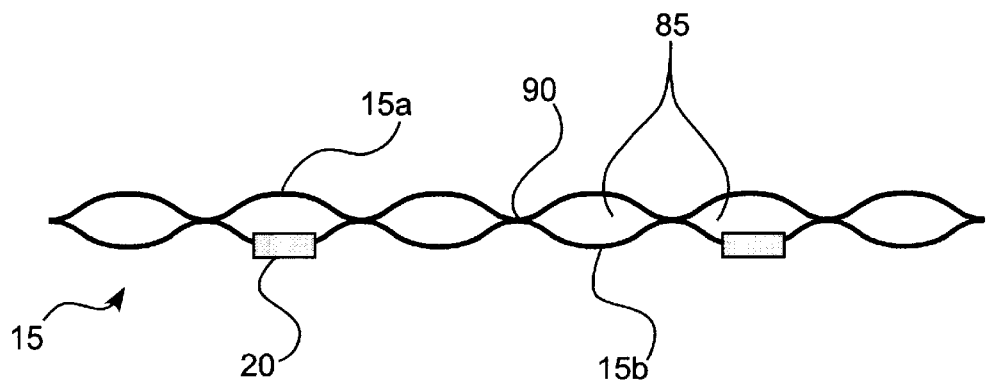

In an exemplary embodiment of the present invention, the removable gel pack member 15 is vertically divided into a plurality of segments 85. (FIG. 4A). The vertical border of each segment is formed by joining the two layers 15a and 15b comprising the major sides of the gel pack to one and the other so as to form a unified plane 90 and to exclude the gel contents at the junction interface. (FIG. 4B). These layers are adjoined by means known to those skilled in the art, including thermal welding or epoxy gluing. The junction so formed should be capable of withstanding the typical thermal and mechanical stresses expected for the removable gel pack 15.

In practice, the predetermined temperature is substantially maintained during application of the portable heating pad to a targeted portion of the anatomy of the subject after attachment of the removable gel pack 15 to the removable heat pad 25 by controlling the application of a current through the electrical heating element 35. Suitable exemplary electrical heating elements include, for example, electrical heating coils typically composed of metallic resistance wire or a conducting polymeric wire, a thin film heating element printed on an insulating surface, such as polyester or mylar, a heating element with a semi-conductor pattern connected to and extending between parallel, spaced apart conductors, or a heating element having a semi-conductor pattern comprising, for example, conductive graphite. The current useful for operating the electrical heating element 35 may be of the alternating current type, such as 120V/60 Hertz household current, for operation in the home or workplace, or of the direct current type, such as 12V current, for convenient portable operation using a battery pack or using a power source in a vehicle, such as an automobile. After attachment of the removable gel pack 15 and the consequent rapid thermal transfer, the operating temperature can be maintained for a longer period of time by heating the heat pad element to the desired temperature before it is disconnected. The thermal storage capabilities of the removable gel pack 15 will allow heat to be delivered for two to three hours after the portable heating pad is disconnected from the power source.

Figure 5:
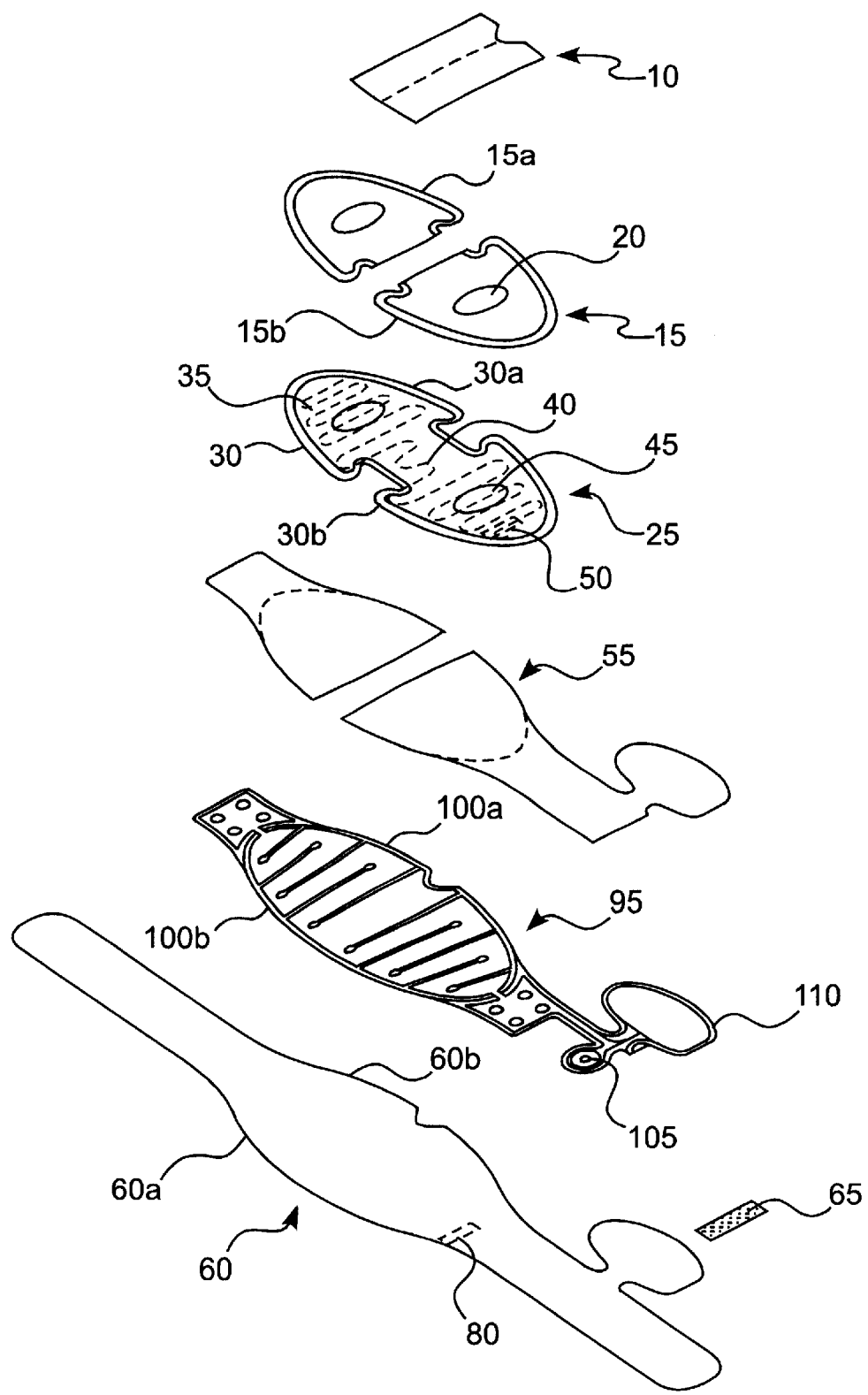
FIG. 5 is a perspective exploded view of an exemplary embodiment of an integrated portable heating pad with removable heat pad and removable gel pack and pressure bladder in accordance with the present invention.

In a further embodiment of the invention shown in FIGS. 5 and 6A–E, an inflatable bladder member 95 may be permanently or removably attached to the outer base member 60. The inflatable bladder member 95 includes, for example, an inner and outer gas-impermeable sheet (100a, 100b). Each sheet 100a, 100b is, for example, shaped to substantially conform to the shape of the wrap. As shown in FIG. 5, each outer base member and gas-impermeable sheet can be designed for a particular anatomical region. For example, FIG. 5 illustrates a contour for the portable heating pad designed for a back. An inlet and internal manual pump 110 integrally formed in the bladder member 95 together permit a variable increase in pressure in the bladder. A controllably sealable outlet 105, such as an externally accessible release valve integrally attached to the bladder 95, permits a variable decrease in pressure within the bladder. The inlet and manual pump 110 can be conveniently constructed, for example, to be integral with the pressure bladder 95. Thus, according to an embodiment of the present invention, an external pump is avoided thereby improving the manufacture and ease of use of the portable heating pad wrap. Manual pumps made of an elastomeric material suited for the purpose are well known in the art. Exemplary manual pumps and controls suitable for use with the integrated structure according to an embodiment of the present invention are, for example, manufactured by Dielectrics Industries of Chicopee, Mass.

Figure 6:
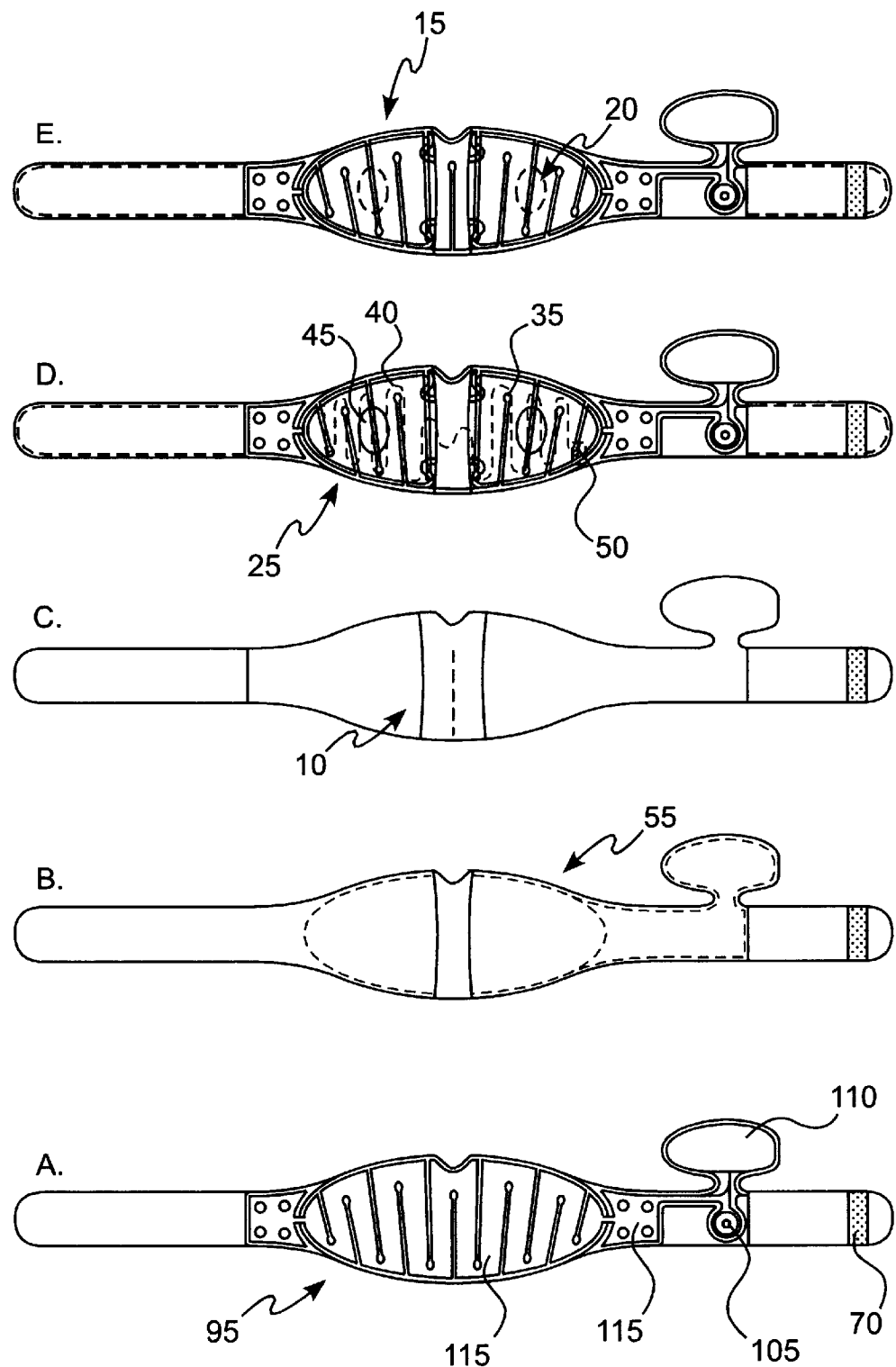
FIGS. 6A–E are a plan view of the stepwise assembly of an exemplary embodiment of an integrated portable heating pad with removable heat pad and removable gel pack and pressure bladder in accordance with the present invention.

The removable heat pad member 25 and removable gel pack member 15 can be releasably attached to the bladder 95 by means of, for example, a heat pad/gel pack pocket member 55. Similar to the embodiment of FIGS. 1A and 1B, the heat pad member 25 and gel pack member 15 can be placed in and stably maintained within the pocket 55 to facilitate contact with the anatomical region of the subject. (FIG. 5). As illustrated in FIGS. 6B and 6C, the heat pad/gel pack pocket 55 (or other suitable retention means) is, for example, permanently attached to the inflatable bladder member 95 and the outer base member 60 by stitching or stapling.

FIGS. 6A–E illustrate the stepwise assembly of an exemplary embodiment of an integrated portable heating pad with removable heat pad and removable gel pack and pressure bladder in accordance with the present invention. The pressure bladder 95 is attached to the outer base member 55 as illustrated in FIG. 6A. The heat pad/gel pack pocket 55 is attached to the outer base member with the attached pressure bladder (FIG. 6A) by stitching or stapling along the lines indicated on the outer base member in FIG. 6B. A flap 10 is attached to the heat pad/gel pack pocket 55 and outer base member 60 with attached pressure bladder 95 along the lines indicated in FIG. 6C. The removable heat pad is inserted into the heat pad/gel pack pocket as indicated in FIG. 6D. The removable gel pack can be attached to the removable heat pad before the removable heat pad is inserted into the heat pad/gel pack pocket as indicated in FIG. 6E.

In an exemplary embodiment, an enclosure or air chamber is formed within the bladder 95 between gas impermeable sheets 100a, 100b and supplied with gas by the integrated pump 110. In further exemplary embodiments of the present invention, the inflatable bladder member 95 includes channels 115 formed within the enclosure. (See FIG. 6A). In alternate embodiments, more than one enclosure could be formed within the bladder 95, each enclosure having channels 115. The channels 115 facilitate the uniform distribution of pressure throughout the bladder 95.

Due to the plurality of channels 115 arranged throughout the bladder, air pressure is spread throughout the bladder 95 and has the effect of substantially compressing the heat pad member 25 and the gel pack member 15 evenly against the targeted anatomical region, thereby substantially enhancing thermal energy transfer between the heat pad member 25 and the gel pack member 15 and the targeted anatomical region. Similarly, due to the inflation of the bladder 95 and the use of channels 115, the thickness of the gel in the gel pack also will be evenly maintained when the portable heating pad is applied against the desired anatomical region, thus improving the transfer of thermal energy from the heat pad member 25 and the gel pack member 15 to the targeted anatomical region. In practice, the inflatable bladder member 95 is typically inflated with any nontoxic inexpensive commonly available gas. Typically, the gas can be air, nitrogen, helium or carbon dioxide. The inflatable bladder member 95 is permanently attached to the outer base member 60 by means known to those skilled in the art, such as stitching or stapling.

The inlet and manual pump 110 can be integrally formed with the bladder 95 and with the outer base member 60 as shown in FIGS. 5 and 6A–E. Further, the inlet and manual pump are positioned for convenient and comfortable access by the user, particularly when the bladder 95 is inflated and placed around an anatomical region. For example, the manual pump is located so as to be easily reached by the user for inflation.

One of skill in the art will readily understand that the present invention is not limited to the specific embodiments shown and described, and may be further used in other applications which will be evident to the ordinarily skilled artisan in the field.

Variations of the invention may be made which are within the scope of the invention as defined in the accompanying claims, without departing from the principles of the invention. It is intended that all matter contained in the above description or shown in the accompanying drawings shall be interpreted as illustrative and not in a limiting sense.

What is claimed is:

1. A portable heating pad comprising:
   an outer base member shaped to conformably cover at least a portion of an anatomical region and having fastening closures so as to provide a releasable securement of the outer base member adjacent the anatomical region;
   a removable heat pad member comprising a cover and electrical heating element, said cover comprising a first layer and a second layer, said first layer being an inner layer, and said second layer being an outer layer, each layer comprising a flexible fabric material and having their perimeter secured together, wherein the electrical heating element is enclosed by the cover and substantially evenly distributed therewithin, said removable heat pad being releasably coupled to the outer base member and releasably coupled to the heating pad electrical power cord; and
   a removal gel pack member releasably attached to said inner layer of the heat pad and comprising a heat-retentive gel which can be heated to a predetermined temperature prior to attachment to the inner layer of the heat pad, wherein said pre-determined temperature is substantially maintained during application to the anatomical region after said attachment.

2. The portable heating pad in accordance with claim 1, wherein the outer base member comprises a resilient filler having an inner and outer cover.

3. The portable heating pad in accordance with claim 2, wherein the resilient filler is a rubber sheet, said rubber sheet comprising at least one of a neoprene, polyurethane and buna rubber.

4. The portable heating pad in accordance with claim 2, wherein the outer cover comprises a heat reflective material.

5. The portable heating pad in accordance with claim 2, wherein the inner cover comprises at least one of a nylon, cotton, cotton/polyester and lycra.

6. The portable heating pad in accordance with claim 1, wherein the fastening closures are of the hook and loop type.

7. The portable heating pad in accordance with claim 1, wherein one of the peripheral edges of the portable heat pad member has a cut-out for a connector for coupling to a detachable electrical power cord.

8. A portable heating pad in accordance with claim 1, wherein the electrical heating element is attached to a connector for coupling to a detachable electrical power cord.

9. A portable heating pad in accordance with claim 8, wherein the electrical heating element comprises at least one of an electrical heating coil composed of a metallic resistance wire or a conducting polymeric wire, a thin film printed on an insulating surface, a semi-conductor pattern connected to and extending between parallel, spaced apart conductors, and a semi-conductor pattern.

10. The portable heating pad in accordance with claim 1, wherein the removable heat pad is releasably maintained within a heat pad/gel pack pocket attached to the outer base member.

11. The portable heating pad in accordance with claim 10, wherein the heat pad/gel pack pocket is attached to the outer base member by stitching or stapling.

12. The portable heating pad in accordance with claim 1, wherein the removable gel pack member can be heated in a thermal heater or in a microwave oven to a predetermined temperature.

13. The portable heating pad in accordance with claim 1, wherein the removable gel pack member contacts and covers substantially the inner layer of the cover of the heat pad member.

14. The portable heating pad in accordance with claim 1, wherein the removable gel pack is releasably attached to the heat pad member by a plurality of fasteners located respectively in complementary positions on the inner layer of the heat pad member and the outer layer of the gel pack member.

15. The portable heating pad in accordance with claim 14, wherein the fasteners are hook and loop type fasteners.

16. The portable heating pad in accordance with claim 1, wherein the removable gel pack member comprises two sheets of a thin liquid-impermeable flexible material selected from a group consisting of vinyl and polyethylene, said sheets forming an inner layer and an outer layer.

17. The portable heating pad in accordance with claim 16, wherein the inner and outer layers of the removable gel pack member are sealed along their respective peripheral edges so as to form a liquid-impermeable junction.

18. The portable heating pad in accordance with claim 1, wherein the removable gel pack member is vertically divided into a plurality of segments.

19. The portable heating pad in accordance with claim 18, wherein each vertical segment border of the removable gel pack member is formed by joining the two layers comprising the major sides of the gel pack to one and the other so as to form a unified plane.

20. The portable heating pad in accordance with claim 1, comprising:
   an inflatable bladder member including an inner and outer gas-impermeable sheet, each sheet being shaped to substantially confirm to a shape of the anatomical region, the inflatable bladder member being attached to the outer base member;
   an inlet; and
   a manual pump integrally formed with the inflatable bladder member.

21. The portable heating pad in accordance with claim 20, wherein the inflatable bladder member further comprises channels formed within an enclosure formed by the gas-impermeable sheets, said channels being capable of directing pressure so as to substantially evenly compress the heat pad member and gel pack member against the anatomical region and thereby substantially enhance thermal energy transfer between the heat pad member and the gel pack member and the anatomical region.

22. The portable heating pad in accord with claim 20, wherein the inflatable bladder member is inflated with a gas including one of air, nitrogen, helium and carbon dioxide.

23. The portable heating pad in accord with claim 20, wherein the inflatable bladder member is attached to the outer base member by stitching or stapling.

24. The portable heating pad in accord with claim 20, wherein said inlet and manual pump are positioned for convenient access.

25. The portable heating pad in accord with claim 20, further comprising a sealable outlet integrally attached to the inflatable bladder, the sealable outlet permitting a variable decrease in pressure in the inflatable bladder.

* * * * *